United States Patent [19]

Mühlbauer

[11] 4,396,117
[45] Aug. 2, 1983

[54] CAPSULE FOR THE STORAGE AND VIBRATION-MIXING OF TWO COMPONENTS PARTICULARLY FOR DENTAL PURPOSES

[75] Inventor: Ernst Mühlbauer, Hamburg, Fed. Rep. of Germany

[73] Assignee: Ernst Muhlbauer KG, Hamburg, Fed. Rep. of Germany

[21] Appl. No.: 326,606

[22] Filed: Dec. 2, 1981

Related U.S. Application Data

[63] Continuation of Ser. No. 197,261, Oct. 15, 1980, Pat. No. 4,306,651, which is a continuation of Ser. No. 51,686, Jun. 25, 1979, abandoned.

[30] Foreign Application Priority Data

Jul. 14, 1978 [DE] Fed. Rep. of Germany ....... 2831005

[51] Int. Cl.³ .............................................. B65D 25/08
[52] U.S. Cl. .................................. 206/219; 206/220; 220/280
[58] Field of Search ................ 206/219, 220; 220/284, 220/285, 286

[56] References Cited

U.S. PATENT DOCUMENTS

| | | | |
|---|---|---|---|
| 1,630,761 | 5/1927 | Prime | 220/284 |
| 3,003,658 | 10/1961 | Lindsey | 220/359 |
| 3,261,457 | 7/1966 | Harmon | 206/219 |
| 3,741,383 | 6/1973 | Wittner | 206/219 |
| 3,815,878 | 6/1974 | Baskas et al. | 206/219 |
| 3,841,467 | 10/1974 | Hansen | 206/219 |
| 3,986,834 | 10/1976 | Steinbrink, Jr. | 206/219 |
| 4,182,447 | 1/1980 | Kay | 206/220 |
| 4,306,651 | 12/1981 | Muhlbauer | 206/219 |

Primary Examiner—Joseph Man-Fu Moy
Attorney, Agent, or Firm—Prutzman, Kalb, Chilton & Alix

[57] ABSTRACT

A capsule for the storage and vibration mixing of two components, particularly for dental uses comprises a mixing chamber in which one of the components is stored, the chamber having an aperture which is closed by means of a removable closure member and a foil bag which can be ruptured without disintegration by the mixing movement is housed in the mixing chamber and contains the other component in liquid form. The liquid component is a high specific gravity liquid such as mercury and the closure member is sealingly secured to that part of the capsule which forms the mixing chamber by a seal which has a predetermined breaking strength, formed conveniently by a weld or adhesive. Externally the closure member presents a cylindrical socket to which can be fitted a cylindrical lever for the purpose of breaking the seal to remove the closure member and allow access to the interior of the mixing chamber for withdrawal of the mix.

3 Claims, 1 Drawing Figure

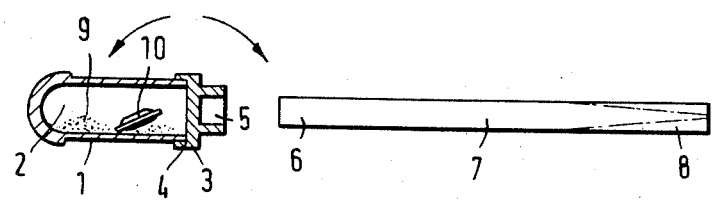

CAPSULE FOR THE STORAGE AND VIBRATION-MIXING OF TWO COMPONENTS PARTICULARLY FOR DENTAL PURPOSES

This is a continuation of application Ser. No. 197,261, filed Oct. 15, 1980, now U.S. Pat. No. 4,306,651, which is a continuation of application Ser. No. 51,686, filed June 25, 1979, now abandoned.

This invention relates to a capsule for the storage and vibration-mixing of two components and is particularly useful for dental purposes.

A multicomponent capsule for dental purposes is already known, wherein a substantially cylindrical section contains a mixing chamber having planar end walls one of which is provided with a small hole, and a hollow cover is attached telescopically at this end and encloses a foil bag. The mixing chamber contains one component, while the foil bag contains the other, liquid component. Before mixing, the cover is pressed against the planar end wall so that the foil bag bursts and pours its contents into the mixing chamber through the small hole. Then the capsule is inserted into a vibration mixer, which moves the capsule backwards and forwards, generally in its longitudinal direction, and thus produces homogenisation of the two components. A disadvantage of this known type of multicomponent capsule is that special manipulation is necessary before mixing, in order to transfer the liquid component to the mixing chamber, and this is often not possible without the use of considerable force.

The present invention is concerned with providing a capsule in which no special manipulation for the transfer of liquid to the mixing chamber is required before the mixing process.

According to the present invention there is provided a capsule for the storage and vibration-mixing of two components comprising a mixing chamber in which one of said components is stored, said chamber having an aperture which is closed by means of a removable closure member and a foil bag which can be reptured without disintegration by the mixing movement housed in said mixing chamber and containing the other of said components in liquid form.

During the vibration mixing, extraordinarily high acceleration forces are exerted on the contents of the capsule. The foil bag can be easily designed in such a manner that it does not adapt to this acceleration, but ruptures or bursts and releases its contents. The smallest of openings in the bag resulting from the rupture is sufficient to empty the liquid contents into the mixing chamber, under the effect of the forces prevailing. There is no difficulty in ensuring that the foil bag opens reliably, by appropriate selection of foil thickness, foil material, arrangement of predetermined breaking strengths, breakable welds and the like. This is particularly simple, if the enclosed liquid is of high specific gravity, such as mercury, since then particularly high forces act on the foil bag during vibration mixing. Disintegration or splintering of the foil bag does not occur, if an appropriate choice is made from the polymeric or elastomeric materials normally used for such a purpose. In many cases, metal foils may also be suitable.

It is already known for one component to be placed in a breakable glass bubble inside the mixing chamber of multicomponent mixer containers. There is, however, the danger that when using a vibration mixer a brittle material such as glass may disintegrate and form many small splinters which could be distributed throughout the mix and make it unsuitable for use. It is a surprising effect, on the contrary, that a soft material such as those normally used for the manufacture of foil bags, does not disintegrate but substantially retains its original size, and can therefore easily be removed from the mix. Because of the different structures and specific gravities of the mix, on the one hand, and the foil bag residue on the other, these are usually separated during the mixing motion, so that it is not necessary to exert any special care when removing the mix, for separation of the foil bag residue.

A further disadvantage of the aforementioned known multicomponent capsules for dental purposes is that even with the best of sealing between that section of the capsule which forms the mixing chamber, and the cover, a certain proportion of the liquid component can escape into the atmosphere during vibration mixing. This is particularly hazardous when mercury is being used as the liquid component. A preferred embodiment of the present invention provides a multicomponent capsule which does not have this disadvantage. For this purpose, the mixing capsule of the embodiment is designed so that the cover or closure member is connected to the section of the capsule which forms the mixing chamber, by means of a seal having a predetermined breaking strength. The closure member and the section of the capsule forming the mixing chamber may be formed as a single unit, or they may be welded or bonded together, in which case the predetermined breaking strength is most conveniently formed in the region of this weld or adhesion. In this way it is possible to guarantee absolute tightness during the vibration mixing. The closure member is easily broken from the section of the capsule which forms the mixing chamber, for opening the capsule and for removing the mix.

Of course, in this respect it is not significant how large the closure member is in relation to the section of the capsule which forms the mixing chamber. The predetermined breaking strength need not be arranged in a seal at one end of the section of the capsule which forms the mixing chamber. It can be provided in any central region of this section of the capsule, and then that part of the capsule which is referred to as the cover, is formed by one half of the capsule section which forms the mixing chamber.

In order to facilitate breakage of the closure member from the remainder of the capsule a lever can be provided, which can be locked onto the closure member as a result of its shape. This lever can be formed in the most simple way, by a cylindrical rod which can be inserted into a corresponding cylindrical socket in the closure member. Of course, the closure member can be fitted initially with an appropriate extension. It is very convenient if the end of the lever is shaped as a spatula.

An embodiment of the present invention will now be described by way of example with reference to the drawing, which shows the capsule in longitudinal section, at about its normal size.

The capsule has a cylindrical section 1, which forms the mixing chamber 2, and is closed at one end by a curved wall. At the other end, the capsule section 1, has an aperture which is closed by a closure member 3. At 4, the section of the capsule which forms the mixing chamber and the closure member, are glued or welded together to form a seal, and this seal is chosen so that sufficient tightness of seal is ensured but the mechanical strength is limited. The closure member 3 has an external extension 5 which is in the form of a cylindrical socket, the bore of which fits the end 6, of a small rod 7. If this is inserted into the extension of the closure member 3, then a bending moment can be exerted about the seal 4, in the direction of the pair of arrows, so that the closure member can be released from the other part of the capsule. The small rod 7, at its end 8, is drawn out to give a wedge-shaped side view (shown as dotted lines), so that it can be used as a spatula for removal of the mix from the chamber 2.

In the mixing chamber 2, are a powder component 9, and a foil bag 10, which may be formed, for example, from two circular foil discs, welded together at the edges to enclose the liquid. For inclusion of mercury this may consist, for example, of two foil discs welded together, each 0.05 mm thick, of polyethylene, polypropylene, polyamid or similar polymeric materials.

I claim:

1. A multi-component dental capsule for separately storing a first liquid mercury component and a second component of a dental amalgam and for selectively mixing the components to compose the dental amalgam, consisting essentially of a rigid capsule housing providing a fully closed mixing chamber containing the said second component, and a closed, rupturable, polymeric foil bag loosely received and freely moveable in the mixing chamber and containing the said liquid mercury component and adapted to be shaken back and forth within the mixing chamber to be ruptured essentially solely by impact with the rigid capsule housing to discharge the liquid mercury component without disintegration of the polymeric foil bag by shaking the rigid capsule housing, the capsule housing having a closure member for removing the dental amalgam after the dental amalgam components are mixed by shaking the capsule housing.

2. A method of separately storing a first liquid mercury component and a second component of a dental amalgam and selectively mixing the components to compose a dental amalgam, comprising the steps of providing a rigid capsule housing, with a housing body having an opening and a removable closure member for the housing body opening, providing a fully closed mixing chamber enclosing the said second component, providing loosely received and freely movable in the mixing chamber a closed, rupturable, polymeric foil bag containing the said liquid mercury component, which can be shaken back and forth within the mixing chamber to be ruptured by impact with the rigid capsule housing to discharge the liquid component without disintegration of the bag by shaking the rigid capsule housing, selectively mixing the two separate components by vigorously shaking the rigid capsule housing sufficiently to shake the polymeric foil bag back and forth to rupture the polymeric foil bag essentially solely by impacting the bag with the rigid capsule housing and mix the said first liquid mercury component with the said second component to form a dental amalgam, removing the housing closure member from the housing body and removing the dental amalgam from the mixing chamber.

3. A method according to claim 2 wherein the housing body and closure member are connected to completely seal the housing body opening, and wherein the closure member is formed with an external lever socket and the housing closure member is removed by inserting a lever into the lever socket and removing the closure member therewith.

* * * * *